(12) United States Patent
Yi et al.

(10) Patent No.: US 11,307,145 B2
(45) Date of Patent: Apr. 19, 2022

(54) OPTICAL DETECTION SYSTEM, BLOOD CELL ANALYZER, AND PLATELET DETECTION METHOD

(71) Applicant: Shenzhen Mindray Bio-Medical Electronics Co., Ltd., Shenzhen (CN)

(72) Inventors: Qiushi Yi, Shenzhen (CN); Dongsheng Wang, Shenzhen (CN); Yong Dai, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/081,757

(22) Filed: Oct. 27, 2020

(65) Prior Publication Data

US 2021/0041364 A1 Feb. 11, 2021

Related U.S. Application Data

(63) Continuation of application No. PCT/CN2019/084509, filed on Apr. 26, 2019.

(30) Foreign Application Priority Data

Apr. 28, 2018 (CN) .......................... 201810405048.9

(51) Int. Cl.
*G01N 21/47* (2006.01)
*G01N 21/64* (2006.01)
*G01N 33/487* (2006.01)

(52) U.S. Cl.
CPC ......... *G01N 21/6486* (2013.01); *G01N 21/47* (2013.01); *G01N 33/487* (2013.01)

(58) Field of Classification Search
CPC .... G01N 21/6486; G01N 21/47; G01N 33/48; G01N 2015/0084
See application file for complete search history.

(56) References Cited

U.S. PATENT DOCUMENTS 3,864,571 A * 2/1975 Stillman ............ G01N 21/6428
250/302
4,336,029 A * 6/1982 Natale ................ G01N 15/1459
250/461.2

(Continued)

FOREIGN PATENT DOCUMENTS

CN 104075976 B 10/2014
CN 104819957 A 8/2015

(Continued)

*Primary Examiner* — Maurice C Smith
(74) *Attorney, Agent, or Firm* — Kory D. Christensen (57) ABSTRACT

An optical detection system, a blood cell analyzer and a platelet detection method are provided. The optical detection system includes: an optical subsystem, a flow chamber and a first detector; the optical subsystem includes a laser, a front optical assembly including an optical isolator, and a rear optical assembly including a blocking diaphragm. The laser is configured to emit a laser beam; the front optical assembly is configured to perform front optical treatment; the rear optical assembly is disposed downstream of the flow chamber in the propagation direction of the laser beam, and is configured to perform rear optical treatment on the scattered light and the laser beam converged at the blocking diaphragm; and the optical isolator is configured to isolate reflected light that is generated when the laser beam passes through the flow chamber.

21 Claims, 5 Drawing Sheets

(56) References Cited

U.S. PATENT DOCUMENTS

| | | | |
|---|---|---|---|
| 4,420,720 A | 12/1983 | Newton et al. | |
| 8,367,358 B2* | 2/2013 | Ting | C09B 23/083 |
| | | | 435/14 |
| 2001/0052763 A1 | 12/2001 | North, Jr. | |
| 2013/0308122 A1* | 11/2013 | Merchez | G01N 21/64 |
| | | | 356/72 |
| 2018/0340881 A1* | 11/2018 | Krockenberger | G01N 15/1459 |

FOREIGN PATENT DOCUMENTS

| | | |
|---|---|---|
| CN | 105181561 A | 12/2015 |
| CN | 106525666 A | 3/2017 |
| CN | 206638566 U | 11/2017 |

\* cited by examiner

OPTICAL DETECTION SYSTEM, BLOOD CELL ANALYZER, AND PLATELET DETECTION METHOD

CROSS-REFERENCE

This application is a continuation of International Application No. PCT/CN2019/084509, filed Apr. 26, 2019, which claims priority benefit of Chinese Patent Application No. 201810405048.9, filed Apr. 28, 2018, the contents of which are incorporated herein by reference.

TECHNICAL FIELD

The disclosure relates to biological inspection technology and, in particular, to an optical detection system, a blood cell analyzer, and a platelet detection method.

BACKGROUND ART

The optical detection system in a blood cell analyzer generally uses a laser as a light source, and the laser is susceptible to reflected light in an optical path and becomes unstable, resulting in amplitude changes, frequency shifts, and/or power peaks, etc.

In practical applications, when power peaks are generated due to unstable oscillation of the laser, they appear in optical forward signals as small pulses, and the amplitudes of these small pulses are much smaller than that of effective signal pulses generated by white blood cell (WBC) particles. Therefore, for WBC optical pulse signal analysis, the pulse detection threshold value is generally set to be greater than the amplitudes of these interfering small pulses to filter out these pulses. However, to deeply analyze the small signal characteristics of the optical pulses to obtain more clinical information, for example, when analyzing platelet (PLT) particles in an optical channel, these interfering small pulses are confused with small pulses generated by normal PLT particles, resulting in the inability to differentiate pulse signals generated by normal PLT from that generated by the interfering small pulses.

SUMMARY OF THE DISCLOSURE

In view of this, embodiments of the present disclosure provide an optical detection system, a blood cell analyzer, and a platelet detection method, which can effectively isolate reflected light generated when laser beams are propagated in an optical path, such that the laser can stably output laser beams, and the detection efficiency of blood cell samples to be tested is improved.

An embodiment of the present disclosure provides a blood cell analyzer, comprising: a sampling part, a reaction part, an optical detection system, an analysis part and an output part, wherein the optical detection system comprises an optical subsystem, a flow chamber and a first detector. The sampling part comprises a sampling needle for collecting a blood sample and conveying the collected blood sample to the reaction part. The reaction part comprises a reaction cell and a reagent supply component, such that the blood sample reacts with a reagent to obtain a test sample solution containing a plurality of platelet particles, and the platelet particles are flowed through the flow chamber one by one.

The optical subsystem comprises a laser, a front optical assembly and a rear optical assembly, and the front optical assembly comprises an optical isolator, wherein the laser is configured to emit a laser beam; the flow chamber is configured to allow the platelet particles to pass through in a line; and the front optical assembly is configured to perform front optical treatment on the laser beam, such that the laser beam subjected to the front optical treatment is converged in a first direction at the platelet particles in the flow chamber, and scattered light is thus generated.

The rear optical assembly is disposed downstream of the flow chamber along the propagation direction of the laser beam, and is configured to perform rear optical treatment on the scattered light, such that the scattered light subjected to the rear optical treatment enters the first detector for light intensity detection. The optical isolator is configured to isolate reflected light from the laser, wherein the reflected light is generated when the laser beam passes through the flow chamber and the rear optical assembly. The analysis part is configured to detect platelet particles flowing through the flow chamber according to light intensity signals of the scattered light obtained by detection of the first detector, and thus obtain a detection result corresponding to the platelet particles. The output part is configured to output the detection result corresponding to the platelet particles.

In the above-mentioned implementation, the optical isolator comprises a beam splitter prism and polarization conversion element which are adhesively connected with each other. The beam splitter prism is configured to reflect the S-polarization component of the incident laser beam and transmit the P-polarization component of the incident laser beam. The polarization conversion element is configured to change the polarization state of the P-polarization component transmitted through the beam splitter prism such that the P-polarization component is changed from linearly polarized light into circularly polarized light, as well as to change the polarization state of the circularly polarized light after reflection into S-polarized light such that the S-polarized light is reflected by the beam splitter prism.

In the above-mentioned implementation, the optical isolator comprises a polarization analyzer and a polarization conversion element which are adhesively connected with each other. The polarization analyzer is configured to allow only the P-polarization component of the laser beam to pass through. The polarization conversion element is configured to change the polarization state of the P-polarization component passing through the polarization analyzer, such that the P-polarization component is changed from linearly polarized light into circularly polarized light, and to change the polarization state of reflected light of the circularly polarized light into S-polarized light such that the S-polarized light is isolated by the polarization analyzer.

In the above-mentioned implementation, the optical isolator comprises a bandpass filter and a frequency-doubling crystal which are adhesively connected with each other. The bandpass filter is configured to allow the laser beam with a wavelength $\lambda$ to pass through. The frequency-doubling crystal is configured to perform frequency doubling on the laser beam passing through the bandpass filter and perform frequency doubling again on reflected light of the frequency-doubled laser beam, such that the reflected light is filtered out by the bandpass filter.

In the above-mentioned implementations, the front optical assembly further comprises a collimating lens. The collimating lens is disposed between the laser and the optical isolator along the propagation direction of the laser beam, and is configured to collimate the laser beam to make the laser beam become a parallel beam.

In the above-mentioned implementations, the rear optical assembly further comprises a blocking diaphragm. The front optical assembly is further configured to perform front optical treatment on the laser beam such that the laser beam subjected to the front optical treatment is converged at the blocking diaphragm in a second direction.

In the above-mentioned implementations, the front optical assembly further comprises a first light converging element and a second light converging element. The first light converging element is configured to perform first focusing on the laser beam, such that the laser beam is converged in the first direction at a detection area of the flow chamber, and scattered light is generated. The second light converging element is configured to perform second focusing on the laser beam such that the laser beam is converged in a second direction at the blocking diaphragm comprised by the rear optical assembly.

In the above-mentioned implementations, the rear optical assembly further comprises a third converging element and an aperture diaphragm. The third converging element is configured to perform third focusing on the scattered light such that the scattered light is converged at the aperture diaphragm and enters the first detector via the aperture of the aperture diaphragm.

In the above-mentioned implementations, the optical detection system further comprises a second detector and/or a fluorescence detector. The second detector is configured to perform light intensity detection on the scattered light which forms an angle within a preset angle range (for example, 60° to 120°) with the propagation direction of the laser beam. The fluorescence detector is configured to detect fluorescence generated by the platelet particles.

In the above-mentioned implementations, the analysis part is further configured to detect the platelet particles in the flow chamber according to at least one of the following information and thus obtain a detection result corresponding to the platelet particles: light intensity signals of the scattered light obtained by detection of the second detector; and fluorescence intensity signals obtained by detection of the fluorescence detector.

In the above-mentioned implementations, the reaction part is further configured to perform hemolysis treatment on the collected blood sample, such that red blood cells in the blood sample are lysed to obtain a test sample solution containing a plurality of platelet particles.

In the above-mentioned implementations, the second direction is perpendicular to the flow direction of the platelet particles; and the first direction is the same as the flow direction of the platelet particles.

In the above-mentioned implementations, the included angle between the propagation direction of the laser beam and the light incident surface of the flow chamber is a non-perpendicular angle.

In the above-mentioned implementations, the laser beam is P-linearly polarized light.

An embodiment of the present disclosure further includes a platelet detection method applied to a blood cell analyzer comprising an optical detection system, wherein the optical detection system comprises a laser, a front optical assembly comprising an optical isolator, a rear optical assembly, a flow chamber, and a first detector; the method comprises: providing a test sample solution containing platelets; making platelet particles in the test sample solution pass through the detection area of the flow chamber one by one; performing front optical treatment on a laser beam emitted by the laser by using the front optical assembly such that the laser beam subjected to the front optical treatment is converged at a detection area of the flow chamber in a first direction, and scattered light is generated when the platelet particles pass through the detection area; performing rear optical treatment on the scattered light by using the rear optical assembly such that the scattered light subjected to the rear optical treatment enters the first detector, wherein reflected light generated when the laser beam passes through the flow chamber is isolated by the optical isolator; and performing light intensity detection on the incident scattered light by using the first detector to obtain a first detection result so as to identify the platelet particles based on the first detection result.

In the above-mentioned implementation, the method further comprises: performing hemolysis treatment on the collected blood sample, such that red blood cells in the blood sample are lysed to obtain a test sample solution containing a plurality of platelet particles. Preferably, in the test sample solution, the scattered light characteristics of fragments obtained by lysing red blood cells are significantly different from that of the platelet particles.

In the above-mentioned implementations, the method further comprises: performing front optical treatment on the laser beam by using the front optical assembly such that the laser beam subjected to the front optical treatment is converged at the blocking diaphragm included by the rear optical assembly in a second direction.

In the above-mentioned implementations, the blood cell analyzer further comprises a second detector; correspondingly, the method further comprises: performing light intensity detection on the scattered light which forms an angle within a preset angle range with the propagation direction of the laser beam to obtain a second detection result, thereby identifying the platelet particles based on the first detection result and the second detection result.

In the above-mentioned implementations, the blood cell analyzer further comprises a fluorescence detector; correspondingly, the method further comprises: performing fluorescence staining treatment on the platelet particles in the test sample solution; further generating fluorescence when the platelet particles in the test sample solution pass through the detection area; and configuring the fluorescence detector to detect the fluorescence generated by the platelet particles to obtain a third detection result, thereby identifying the platelet particles based on the first detection result and the third detection result.

In the above-mentioned implementations, the blood cell analyzer further comprises a second detector and a fluorescence detector; correspondingly, the method further comprises: performing fluorescence staining treatment on the platelet particles in the test sample solution; further generating fluorescence when the platelet particles in the test sample solution pass through the detection area; configuring the second detector to perform light intensity detection on the scattered light which forms an angle within a preset angle range with the propagation direction of the laser beam to obtain a second detection result; configuring the fluorescence detector to detect fluorescence generated by the platelet particles to obtain a third detection result; identifying the platelet particles according to the first detection result and the third detection result; identifying white blood cell particles, and/or counting white blood cells, and/or differentiating white blood cells to obtain white blood cell subpopulations at least including monocytes, lymphocytes, and neutrophils, according to the second detection result and the third detection result.

An embodiment of the present disclosure further provides an optical detection system, comprising an optical subsystem, a flow chamber, and a first detector. The optical subsystem comprises a laser, a front optical assembly comprising an optical isolator, and a rear optical assembly comprising a blocking diaphragm, wherein the laser is configured to emit a laser beam. The front optical assembly is configured to perform front optical treatment on the laser beam, and the laser beam subjected to the front optical treatment is converged in a second direction at the blocking diaphragm and is converged in a first direction at a blood cell sample to be tested in the flow chamber, and scattered light is thus generated. The rear optical assembly is disposed downstream of the flow chamber along the propagation direction of the laser beam, and is configured to perform rear optical treatment on the scattered light and the laser beam which is converged at the blocking diaphragm, such that the scattered light subjected to the rear optical treatment enters the first detector for light intensity detection. The optical isolator is configured to isolate reflected light generated when the laser beam passes through the flow chamber and the rear optical assembly.

In the above-mentioned implementation, the optical isolator comprises a beam splitter prism and polarization conversion element which are adhesively connected with each other. The beam splitter prism is configured to reflect the S-polarization component of the incident laser beam and transmit the P-polarization component of the incident laser beam. The polarization conversion element is configured to change the polarization state of the P-polarization component transmitted through the beam splitter prism such that the P-polarization component is changed from linearly polarized light into circularly polarized light, as well as to change the polarization state of the circularly polarized light after reflection into S-polarized light such that the S-polarized light reflected by the beam splitter prism.

In the above-mentioned implementation, the optical isolator comprises a polarization analyzer and a polarization conversion element which are adhesively connected with each other. The polarization analyzer is configured to allow only the P-polarization component of the laser beam to pass through. The polarization conversion element is configured to change the polarization state of the P-polarization component passing through the polarization analyzer, such that the P-polarization component is changed from linearly polarized light into circularly polarized light, and to change the polarization state of reflected light of the circularly polarized light into S-polarized light such that the S-polarized light isolated by the polarization analyzer.

In the above-mentioned implementations, when the laser beam is incident to the optical isolator perpendicularly, the reflectivity of the first incident surface of the beam splitter prism is not greater than 0.5%.

In the above-mentioned implementations, the optical isolator comprises a bandpass filter and a frequency doubling crystal which are adhesively connected with each other. The bandpass filter is configured to allow the laser beams with a wavelength A to pass through. The frequency-doubling crystal is configured to perform frequency doubling on the laser beam passing through the bandpass filter and perform frequency doubling again on reflected light of the frequency-doubled laser beam, such that the reflected light is filtered out by the bandpass filter.

In the above-mentioned implementations, the front optical assembly further comprises a collimating lens. The collimating lens is disposed between the laser and the optical isolator along the propagation direction of the laser beam, and is configured to collimate the laser beam to make the laser beam become a parallel beam.

In the above-mentioned implementations, the front optical assembly further comprises a first light converging element and a second light converging element. The first light converging component is configured to perform first focusing on the laser beam such that the laser beam is converged in the first direction at the blood cell sample to be tested in the flow chamber, and scattered light is generated. The second light converging element is configured to perform second focusing on the laser beam such that the laser beam is converged in the second direction at the blocking diaphragm.

In the above-mentioned implementations, the rear optical assembly further comprises a third converging element and an aperture diaphragm. The third converging component is configured to perform third focusing on the scattered light such that the scattered light is converged at the aperture diaphragm and enters the first detector via the aperture of the aperture diaphragm.

In the above-mentioned implementations, the optical detection system further comprises a second detector and a fluorescence detector. The second detector is configured to perform light intensity detection the scattered light which forms an angle within a preset angle range (for example, 60° to 120°) with the propagation direction of the laser beam; and the fluorescence detector is configured to perform fluorescence detection on fluorescence generated by the blood cell sample to be tested.

In the above-mentioned implementations, the second direction is perpendicular to the flow direction of the blood cell sample to be tested; and the first direction is the same as the flow direction of the blood cell sample to be tested.

In the above-mentioned implementations, the optical isolator has an optical isolation degree not smaller than 30 db.

In the above-mentioned implementations, the blocking diaphragm has a light collection angle of 1-10°.

In the above-mentioned implementations, the laser beam has a wavelength of 630 nm to 640 nm.

In the above-mentioned implementations, the laser beam is P-linearly polarized light.

By applying the optical detection system, the blood cell analyzer and the platelet detection method of the above-mentioned embodiments of the present disclosure, reflected light generated when a laser beam is propagated in an optical path can be commendably isolated, such that the laser can stably output a laser beam, thereby avoiding small pulses occurring due to power peaks generated when the reflected light enters the laser, also avoiding confusion between those interfering small pulses and small pulses generated by platelet particles, and significantly improving the detection precision of the blood cell analyzer.

DETAILED DESCRIPTION OF EMBODIMENTS

The present disclosure will be further described below in detail in combination with the accompanying drawings and the embodiments. It should be understood that the embodiments provided herein are only for explaining the present disclosure, but not for limiting the present disclosure. In addition, the embodiments provided below are a part of embodiments for implementing the present disclosure, but not all embodiments. And in a non-conflict case, the technical solutions recorded in the embodiments of the present disclosure can be implemented in an arbitrary combination way.

It should be noted that, in the embodiments of the present disclosure, the term 'include', 'comprise', or any other variant is intended to cover a non-exclusive meaning, such that a method or a device comprising a series of elements not only comprises expressly recorded elements but also comprises other elements not expressly listed, or further comprises inherent elements for implementing the method or device. Without further restrictions, the elements defined by the sentence 'comprising a' do not exclude other relevant elements (for example, steps in a method or units in a device, herein the units may be some circuits, some processors, some programs, or software, etc.) which are further comprised in the method or device comprising the elements.

It should be noted that, the terms 'first/second/third/' related to the embodiments of the present disclosure are only for distinguishing similar objects rather than representing specific sequence of the aimed objects, and it can be understood that 'first/second/third/' are interchangeable in a specific sequence or a precedence order under allowable conditions. It should be understood that the objects distinguished by 'first/second/third/' are interchangeable under proper conditions such that the embodiments of the present disclosure described herein can be implemented in a sequence excluding those shown in the drawings or described herein.

During research, the inventors have discovered that, in order to prevent reflected light from being fed back to the laser, a magneto-optical device based on the Faraday effect can be used as an optical isolator and placed in the optical path. This isolator has a relatively large mechanical size and generally can only be placed outside a light source assembly, while the light beam outside the light source assembly is non-parallel light, and when non-parallel light enters the optical isolator, the optical isolation effect of the optical isolator will be seriously weakened. Therefore, this solution has the disadvantages of large size, high cost, and poor isolation effect.

In an embodiment of the present disclosure, the optical detection system comprises an optical subsystem, a flow chamber and a first detector, and the optical subsystem comprises a laser, a front optical assembly comprising an optical isolator, and a rear optical assembly comprising a blocking diaphragm, wherein the laser is configured to emit a laser beam; the front optical assembly is configured to perform front optical treatment on the laser beam, such that the laser beam subjected to the front optical treatment is converged at the blocking diaphragm in a second direction and is converged in a first direction at a blood cell sample to be tested in the flow chamber, and scattered light is thus generated; the rear optical assembly is disposed downstream of the flow chamber along the propagation direction of the laser beam, and is configured to perform rear optical treatment on the scattered light and the laser beam which is converged at the blocking diaphragm, such that the scattered light subjected to the rear optical treatment enters the first detector for light intensity detection; and the optical isolator is configured to isolate reflected light generated when the laser beam passes through the flow chamber and the rear optical assembly.

An optical detection system provided by an embodiment of the present disclosure will be described in detail.

Figure 1:
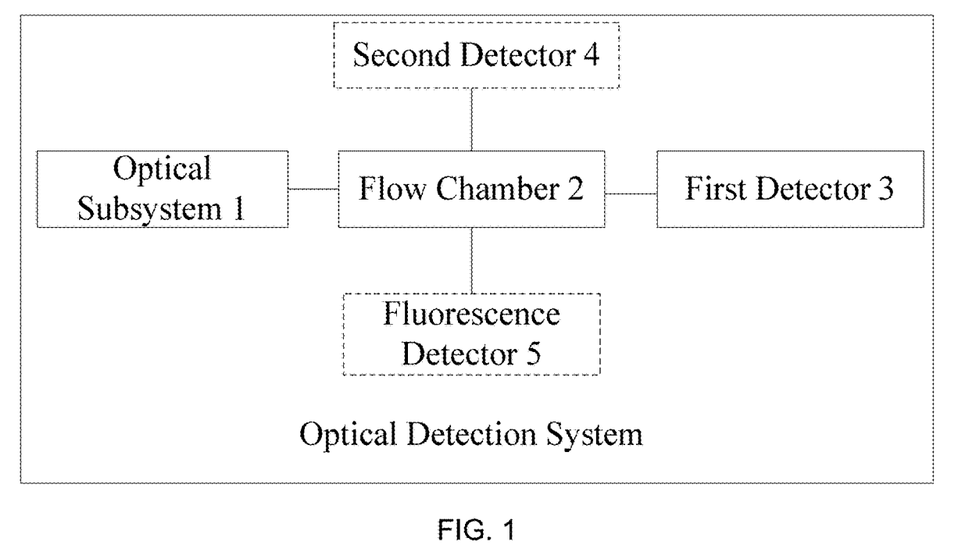
FIG. 1 illustrates a schematic structure diagram I of an optical detection system provided by an embodiment of the present disclosure.
Figure 2:
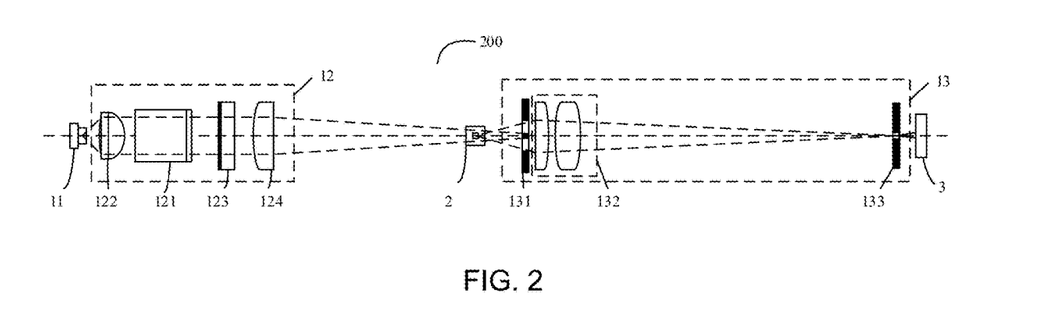
FIG. 2 illustrates a schematic structure diagram II of an optical detection system provided by an embodiment of the present disclosure.

FIG. 1 is a schematic structure diagram I of an optical detection system provided by an embodiment of the present disclosure, and FIG. 2 is a schematic structure diagram II of an optical detection system 200 provided by an embodiment of the present disclosure. With reference to FIG. 1 and FIG. 2, the optical detection system 200 provided by the embodiment of the present disclosure comprises an optical subsystem 1, a flow chamber 2, and a first detector 3.

The optical subsystem 1 comprises a laser 11, a front optical assembly 12 comprising an optical isolator 121, and a rear optical assembly 13 comprising a blocking diaphragm 131, wherein the laser 11 is configured to emit a laser beam; the front optical assembly 12 is configured to perform front optical treatment on the laser beam, such that the laser beam subjected to the front optical treatment is converged at the blocking diaphragm 131 in a second direction, and is converged in a first direction at a blood cell sample to be tested in the flow chamber 2, and scattered light is thus generated; the rear optical assembly 13 is disposed downstream of the flow chamber 2 along the propagation direction of the laser beam, and is configured to perform rear optical treatment on the scattered light and the laser beam converged at the blocking diaphragm 131, such that the scattered light subjected to the rear optical treatment enters the first detector 3 for light intensity detection; and the optical isolator 121 is configured to isolate reflected light generated when the laser beam passes through the flow chamber and the rear optical assembly.

Next, the laser 11 in the optical subsystem will be described. In an embodiment, the laser 11 is a semiconductor laser. In a practical implementation, the laser 11 may be a P-linearly polarization laser. In practical applications, the wavelength of the laser beam emitted by the laser determines the design of the main parameters of the optical path, such as model selection of a lens, the selection of signal collection angle and the like, and the wavelength of the laser beam is also related to the reagents such as fluorescence dyes used in the detection. In an embodiment, the wavelength of laser beam emitted by the laser 11 is within 630 nm to 640 nm.

Next, each part of the front optical assembly 12 in the optical subsystem will be described. In an embodiment, the optical isolator 121 in the front optical assembly 12 comprises a beam splitter prism and a polarization conversion element which are adhesively connect with each other. The beam splitter prism is configured to reflect the S-polarization component of the incident laser beam and transmit the P-polarization component of the incident laser beam. The polarization conversion element is configured to change the polarization state of the P-polarization component transmitted through the beam splitter prism such that the P-polarization component is changed from linearly polarized light into circularly polarized light, as well as to change the polarization state of the circularly polarized light after reflection into S-polarized light such that the S-polarized light is reflected by the beam splitter prism.

Figure 3:
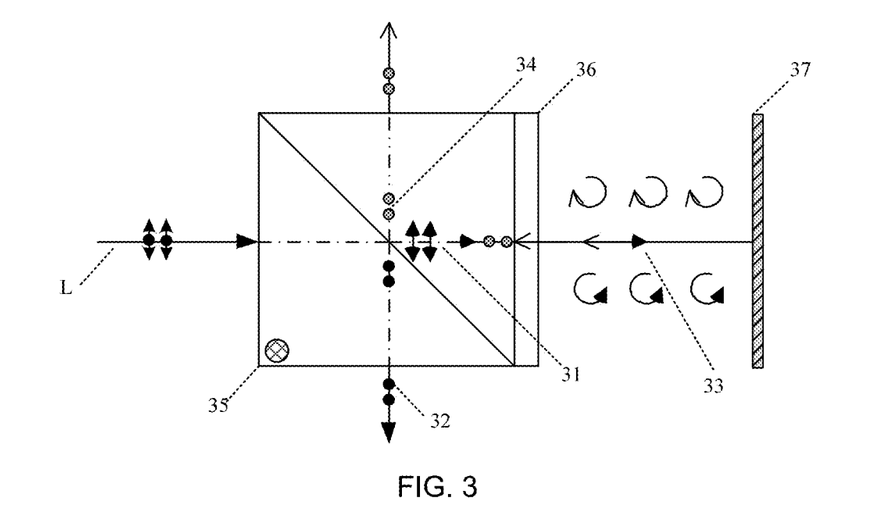
FIG. 3 illustrates a principle diagram of an optical isolator provided by an embodiment of the present disclosure.

The polarization conversion element is a quarter wave plate, which is taken as an example, as shown in FIG. 3. FIG. 3 is a principle diagram of an optical isolator provided by an embodiment of the present disclosure. When laser beam L (TM mold) enters the beam splitter prism 35 perpendicularly, the P-polarized light 31 (namely the polarization component parallel to the plane of the drawing) in the laser beam L can pass through the beam splitter prism 35, while the S-polarized light 32 (namely the polarization component perpendicular to the plane of the drawing) in the laser beam L is reflected by a 45-degree bevel of the beam splitter prism 35. Afterwards, the P-polarized light 31 passes through the quarter wave plate 36, and the polarization state of the P-polarized light 31 passing through the quarter wave plate 36 is changed from linearly polarized light into circularly polarized light 33; the reflected light (reflected light reflected by the downstream optical path 37) of the circularly polarized light 33 passes through the quarter wave plate 36 again and the polarization state is changed from circularly polarized light into S-polarized light 34, and the S-polarized light 34 will be reflected by the 45-degree bevel of the beam splitter prism 35 without being fed back to the laser, thereby realizing the isolation of the reflected light in the optical path.

Figure 4:
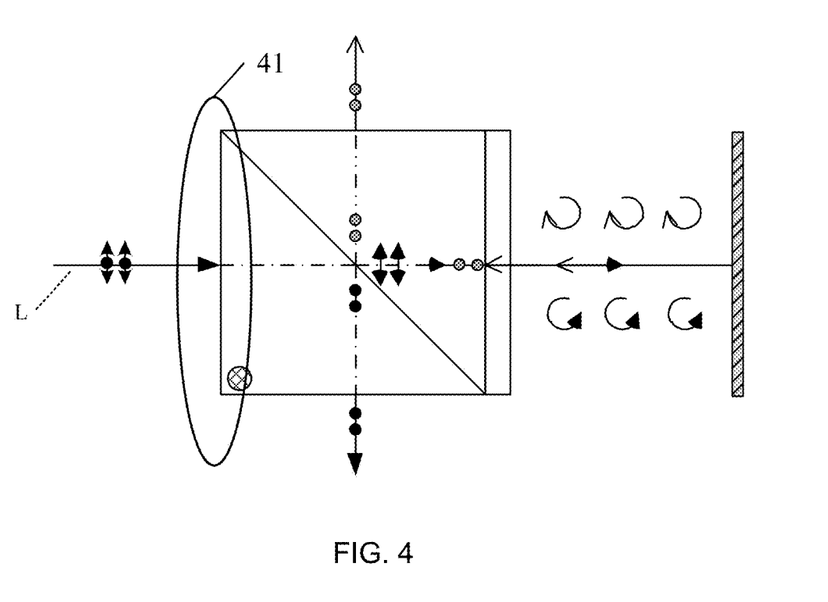
FIG. 4 illustrates a schematic diagram of a first incident surface of an optical isolator provided by an embodiment of the present disclosure.

In practical applications, when the laser beam is perpendicularly incident to the optical isolator, the reflectivity of the first incident surface of the beam splitter prism is not greater than 0.5%, or not greater than 0.1%, or not greater than 0.05%. The first incident surface is shown in FIG. 4. FIG. 4 is a schematic diagram of the first incident surface of an optical isolator provided by an embodiment of the present disclosure, wherein the reference number 41 represents the first incident surface. In a practical implementation, the light reflectivity of the first incident surface can be achieved by the coating design and process of the first incident surface.

In an embodiment, the optical isolator 121 may also comprise a polarization analyzer and a polarization conversion element which are adhesively connected with each other. The polarization analyzer is configured to allow only the P-polarization component of the laser beam to pass through. The polarization conversion element is configured to change the polarization state of the P-polarization component passing through the polarization analyzer such that the P-polarization component is changed from linearly polarized light into circularly polarized light, as well as to change the polarization state of reflected light of the circularly polarized light after reflection into S-polarized light such that the S-polarized light is isolated by the polarization analyzer.

As an example, the polarization conversion element is a magneto-optical crystal. When the laser beam enters the polarization analyzer, only the P-polarized light in the laser beam can pass through the polarization analyzer. After the P-polarized light passing through the polarization analyzer enters the magneto-optical crystal, the polarization state of the P-polarized light passing through the magneto-optical crystal is changed, and the polarization direction of the P-polarized light is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light such that the S-polarized light is isolated by the polarization analyzer without being fed back to the laser.

In practical applications, the polarization conversion element may also be a rotary optical crystal. In practical applications, the beam splitter prism and the polarization analyzer can be combined with any one of the quarter wave plate, the magneto-optical crystal and the rotary optical-crystal to achieve the isolation of the reflected light in the optical path.

In an embodiment, the optical isolator 121 comprises a bandpass filter and a frequency doubling crystal which are adhesively connected with each other. The bandpass filter is configured to allow the laser beam with a wavelength A to pass through. The frequency-doubling crystal is configured to perform frequency doubling on the laser beam passing through the bandpass filter and perform frequency doubling again on reflected light of the frequency-doubled laser beam, such that the reflected light is filtered out by the bandpass filter.

In an embodiment, the optical isolator has an optical isolation degree not smaller than 30 db.

In an embodiment, the front optical assembly 12 further comprises a collimating lens 122. The collimating lens 122 is disposed between the laser 11 and the optical isolator 121 along the propagation direction (the direction of the optical axis) of the laser beam, and is configured to collimate the laser beam to make the laser beam become a parallel beam. In an embodiment, the front optical assembly 12 further comprises a first light converging element 123 and a second light converging element 124. The first light converging element 123 is configured to perform first focusing on the laser beam such that the laser beam is converged in the first direction at the blood cell sample to be tested in the flow chamber, and the scattered light is thus generated. The second light converging element 124 is configured to perform second focusing on the laser beam such that the laser beam is converged at the blocking diaphragm 131 in the second direction.

In practical applications, the second direction is the transverse direction, namely a direction perpendicular to the flow direction of the blood cell sample to be tested; and the first direction is the longitudinal direction, namely a direction the same as the flow direction of the blood cell sample to be tested. In practical applications, the first light converging element 123 and the second light converging element 124 may be implemented by cylindrical lenses with different optical parameters (such as focal length, etc.), for example, the first light converging element 123 is implemented by a first cylindrical lens, and the second light gathering component 124 is implemented by a second cylindrical lens.

Figure 5:
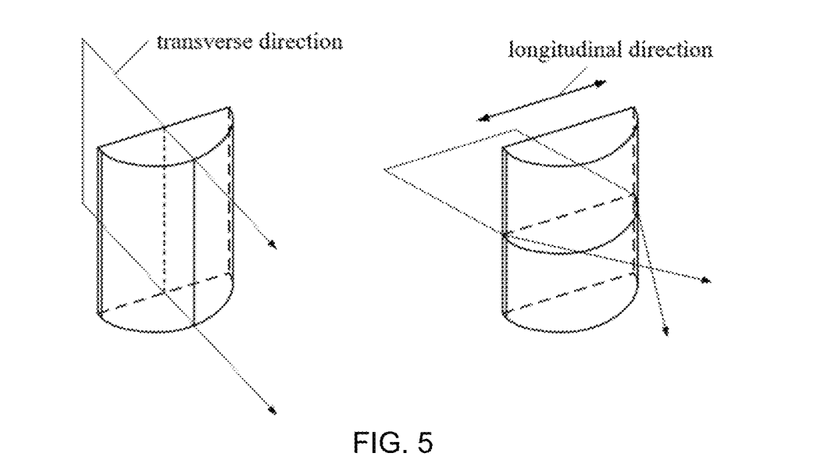
FIG. 5 illustrates a light converging schematic diagram of a second cylindrical lens provided by an embodiment of the present disclosure.

The second light converging element 124 is a second cylindrical lens, which is taken as an example for description, as shown in FIG. 5. FIG. 5 is a light converging schematic diagram of a second cylindrical lens provided by an embodiment of the present disclosure. The laser beam passes through the second cylindrical lens and is not treated in the longitudinal direction by the second cylindrical lens; the laser beam passing through the second cylindrical lens is compressed in the transverse direction and is focused in the transverse direction (perpendicular to the flow direction of the blood cell sample to be tested); and the laser beam is focused at the blocking diaphragm in the embodiment of the present disclosure.

Figure 6:
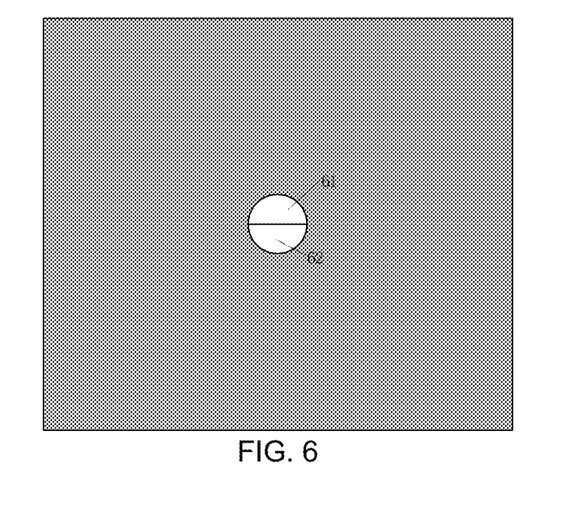
FIG. 6 illustrates a front view of a blocking diaphragm provided by an embodiment of the present disclosure.

Next, each part of the rear optical assembly 13 will be described, as shown in FIG. 6. FIG. 6 is a front view of a blocking diaphragm provided by an embodiment of the present disclosure. The laser beam irradiated on the blood cell sample in the flow chamber is scattered, and the generated scattered light is collected by the blocking diaphragm. In a practical implementation, the blocking diaphragm is used to restrict the collection angle of low-angle scattering signals and the blocking diaphragm is also used to stop the laser beam converged at the blocking diaphragm in the second direction. In an embodiment, the light collection angle of the blocking diaphragm may be 1-10°.

In an embodiment, the rear optical assembly 13 further comprises a third converging element 132 and an aperture diaphragm 133. The third converging element 132 is configured to perform third focusing on the scattered light such that the scattered light is converged at the aperture diaphragm and enters the first detector via the aperture of the aperture diaphragm, for light intensity detection.

In an embodiment, the third converging element may be one of the following:

a lens assembly including at least one plano-convex lens and at least one biconvex lens;

a lens assembly including at least two plano-convex lenses;

a lens assembly including at least two biconvex lenses;

a lens assembly including at least two spherical lenses; and an aspherical lens.

In an embodiment, the optical detection system further comprises a second detector 4 and a fluorescence detector 5. The second detector is disposed in a direction which forms an angle within a preset angle range with the propagation direction of the laser beam, and is configured to perform light intensity detection on the scattered light which forms an angle within the preset angle range with the propagation direction of the laser beams. The fluorescence detector is disposed in a direction which forms an angle within a preset angle range with the propagation direction of the laser beam, and is configured to perform fluorescence detection on fluorescence generated by the blood cell sample to be tested.

Figure 7:
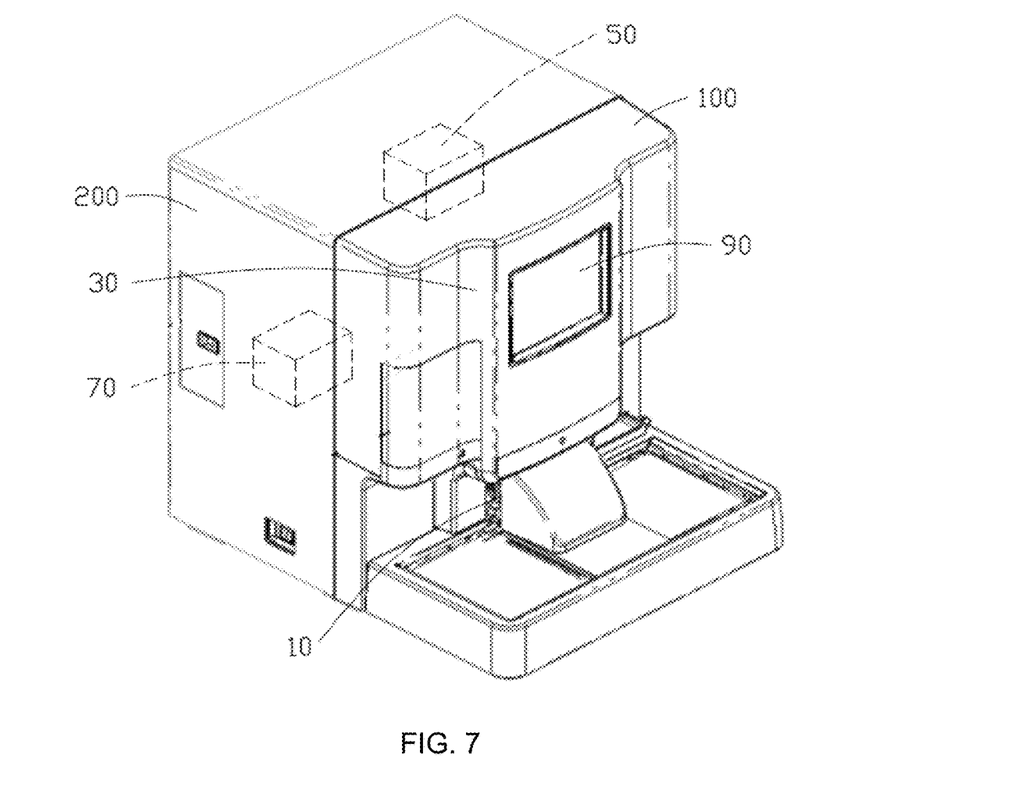
FIG. 7 illustrates a schematic structure diagram of a blood cell analyzer provided by an embodiment of the present disclosure.

Next, a blood cell analyzer provided by an embodiment of the present disclosure will be described, and FIG. 7 is a schematic structure diagram of a blood cell analyzer 700 provided by an embodiment of the present disclosure. The blood cell analyzer 700 comprises a first housing 100, a second housing 200, a sampling part 10, a reaction part 30, an optical detection system 50, an analysis part 70 and an output part 90. In practical applications, the output part 90 may be a user interface. In this embodiment, the optical detection system 50 and the analysis part 70 are disposed inside the second housing 200, and are disposed on two sides of the second housing 200, respectively. The reaction part 30 is disposed inside the first housing 100, and the output part 90 and the sampling part 10 are disposed on outer surface of the first housing 100.

The optical detection system 50 may include an optical subsystem, a flow chamber and a first detector. The sampling part 10 comprises a sampling needle for collecting a blood sample and conveying the collected blood sample to the reaction part. The reaction part 30 comprises a reaction cell and a reagent supply component and provides a reaction place for the blood sample to react with a reagent to obtain a test sample solution containing a plurality of platelet particles. The reaction part further comprises a pipeline and a drive component, such as an injector, an air pump, etc., such that the platelet particles are flowed through the flow chamber one by one.

The optical subsystem comprises a laser, a front optical assembly and a rear optical assembly, and the front optical assembly comprises an optical isolator, wherein the laser comprises a light source and is used to emit a laser beam; the flow chamber allows platelet particles to pass through in a line; the front optical assembly is configured to perform front optical treatment on the laser beam, and the laser beam subjected to the front optical treatment is converged in a first direction at the platelet particles in the flow chamber, and scatter light is thus generated; the rear optical assembly is disposed downstream of the flow chamber along the propagation direction of the laser beam, and is configured to perform rear optical treatment on the scattered light, such that the scattered light subjected to the rear optical treatment enters the first detector for light intensity detection; the optical isolator is configured to isolate reflected light from the laser; wherein the reflected light is generated when the laser beam passes through the flow chamber and the rear optical assembly; the analysis part 70 is configured to detect platelet particles flowing through the flow chamber according to light intensity signals of the scattered light obtained by detection of the first detector to obtain a detection result corresponding to the platelet particles; the output part 90 is configured to output the detection result corresponding to the platelet particles.

Next, each part included by the optical detection system 50 of the blood cell analyzer 700 will be described.

Figure 8:
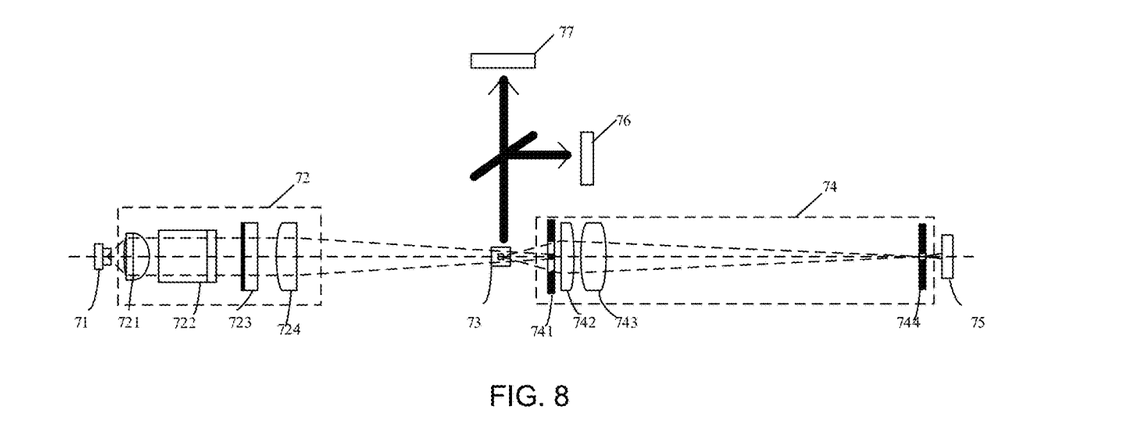
FIG. 8 illustrates a schematic structure diagram III of an optical detection system provided by an embodiment of the present disclosure.

FIG. 8 is a schematic structure diagram of an optical detection system provided by an embodiment of the present disclosure. As shown in FIG. 8, the optical detection system provided by the embodiment of the present disclosure comprises a laser 71, a front optical assembly 72, a flow chamber 73, and a rear optical assembly 74, a forward detector 75, a side detector 76, and a fluorescence detector 77.

In practical applications, the platelet particles pass through the flow chamber and are detected (such as detected in terms of light intensity), counted, etc. In this embodiment, the flow direction of platelet particles is a direction perpendicular to the plane of the drawing, and the propagation direction of the laser beam emitted by the laser 71 is a direction parallel to the plane of drawing.

In a practical implementation, the laser 71 is a P-linearly polarization laser, and the wavelength of the laser beam emitted by the laser 71 is within 630 nm to 640 nm.

As shown in FIG. 8, the front optical assembly 72 comprises a collimating lens 721, an optical isolator 722, a first cylindrical lens 723 and a second cylindrical lens 724 that are sequentially disposed in the propagation direction of the laser beam. The rear optical assembly 74 comprises a blocking diaphragm 741, a plano-convex lens 742, a biconvex lens 743 and an aperture diaphragm 744 that are sequentially disposed in the propagation direction of the laser beam.

The laser beam emitted by the laser 71 is collimated by the collimating lens 721 to become a parallel laser beam, then passes through the optical isolator 722, and is focused at the center of the flow chamber 73 in the longitudinal direction (perpendicular to the plane of drawing) by the first cylindrical lens 723 to form a detection light spot. The included angle between the propagation direction of the laser beam and the light incident surface of the flow chamber is a right angle. The laser beam focused at the flow chamber is irradiated on the platelet particles in the flow chamber and is thus scattered. After being compressed in the longitudinal direction by the first cylindrical lens 723, the size of the laser beam in the longitudinal direction is matched with that of the platelet particles. The laser beam passing through the first cylindrical lens 723 enters the second cylindrical lens 724, and is compressed in the transverse direction (parallel to the plane of drawing), and is converged in the transverse direction at the blocking diaphragm 741.

Wherein the scattered light generated by the platelet particles irradiated in the flow chamber is collected by the blocking diaphragm such that the scattered light is focused by a lens assembly consisting of the plano-convex lens 742 and the lenticular lens 743, then converged at the aperture diaphragm 744 and enters the forward detector 75 via the aperture of the aperture diaphragm 744 so as to be detected in terms of forward light signal intensity by the forward detector 75.

In practical applications, as shown in FIG. 8, the side detector 76 and the fluorescence detector 77 are disposed along a direction perpendicular to the propagation direction of the laser beam, wherein the side detector 76 is configured to perform light intensity detection on the scattered light perpendicular to the propagation direction of the laser beam, and the fluorescence detector 77 is disposed along a direction perpendicular to the propagation direction of the laser beam and is configured to perform fluorescence detection on the scattered light.

In a practical implementation, the laser beam emitted by the laser 71 will be reflected when propagating in the optical path shown in FIG. 8, and the optical isolator 722 is configured to isolate the reflected light generated by the laser beam emitted by the laser 71 when the laser beam propagates in the optical path.

In an embodiment, the optical isolator 722 comprises a beam splitter prism and a quarter wave plate which are adhesively connected with each other. The beam splitter prism is configured to reflect the S-polarization component of the incident laser beam and transmit the polarization-polarization component of the incident laser beam. The quarter wave plate is configured to change the polarization state of the P-polarization component transmitted through the beam splitter prism such that the P-polarization component is changed from linearly polarized light into circularly polarized light, as well as to change the polarization state of the circularly polarized light after reflection into S-polarized light such that the S-polarized light is reflected by the beam splitter prism.

When laser beam enters the beam splitter prism perpendicularly, the P-polarized light (namely the polarization component parallel to the plane of the drawing) in the laser beam can pass through the beam splitter prism, while the S-polarized light (namely the polarization component perpendicular to the plane of the drawing) in the laser beam is reflected by a 45-degree bevel of the beam splitter prism; afterwards, the P-polarized light passes through the quarter wave plate, and the polarization state of the P-polarized light passing through the quarter wave plate is changed from linearly polarized light into circularly polarized light; the reflected light (reflected light reflected by the downstream optical path) of the circularly polarized light passes through the quarter wave plate again, and the polarization state is change from the circularly polarized light to S-polarized light; and the S polarized light will be reflected by the 45-degree bevel of the beam splitter prism without being fed back to the laser, thereby realizing the isolation of the reflected light in the optical path.

In practical applications, when the laser beam enters the optical isolator perpendicularly, the reflectivity of the first incident surface of the beam splitter prism is not greater than 0.5%. Herein, the first incident surface is shown in FIG. 4. FIG. 4 is a schematic diagram of a first incident surface of an optical isolator provided by an embodiment of the present disclosure, wherein the surface represented by the reference number 41 is the first incident surface. In a practical implementation, the light reflectivity of the first incident surface can be achieved by the coating design and process of the first incident surface.

In an embodiment, the optical isolator 121 may also comprise a polarization analyzer and a polarization conversion element which are adhesively connected with each other. The polarization analyzer is configured to allow only the P-polarization component of the laser beam to pass through. The magneto-optical crystal is configured to change the polarization state of the P-polarization component passing through the polarization analyzer such that the polarization direction of the P-polarization component is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light such that the S-polarized light is isolated by the polarization analyzer.

When the laser beam enters the polarization analyzer, only the P-polarized light in the laser beam can pass through the polarization analyzer, the P-polarized light passing through the polarization analyzer enters the magneto-optical crystal, the polarization state of the P-polarized light passing through the magneto-optical crystal is changed, and the polarization direction of the P-polarized light is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light such that the S-polarized light is isolated by the polarization analyzer without being fed back to the laser.

In an embodiment, the optical isolator may further comprise a bandpass filter and a frequency doubling crystal which are adhesively connected with each other. The bandpass filter is configured to allow the laser beam with a wavelength A to pass through. The frequency-doubling crystal is configured to perform frequency doubling on the laser beam passing through the bandpass filter and perform frequency doubling again on reflected light of the frequency-doubled laser beam, such that the reflected light is filtered out by the bandpass filter.

In an embodiment, the optical isolator has an optical isolation degree not smaller than 30 db.

Figure 9:
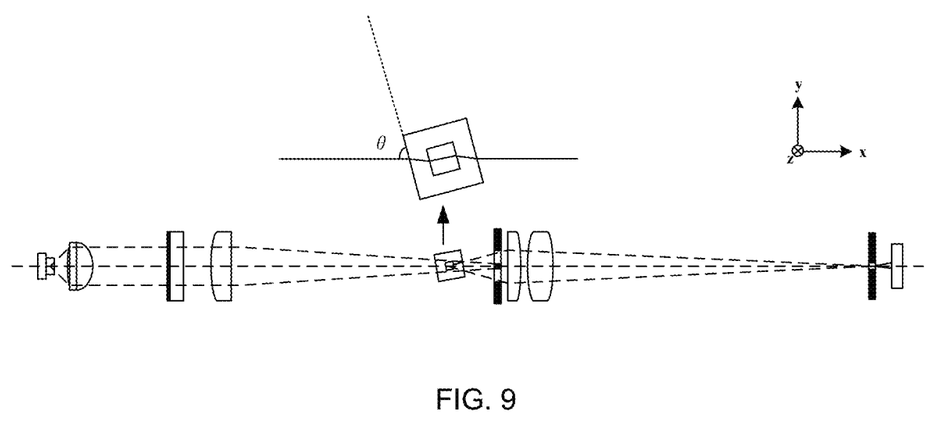
FIG. 9 illustrates a schematic structure diagram IV of an optical detection system provided by an embodiment of the present disclosure.

In an embodiment, the included angle between the propagation direction of the laser beam and the light incident surface of the flow chamber may be a non-perpendicular angle, namely the position of the flow chamber in the above-mentioned embodiments is deflected by a certain angle in the x-y plane, namely in the plane of drawing such that the flow chamber is obliquely disposed. FIG. 9 is a schematic structure diagram of an optical detection system provided by an embodiment of the present disclosure. As shown in FIG. 9, the included angle θ between the propagation direction of the laser beam and the light incident surface of the flow chamber is an acute angle. In an embodiment, the angle θ ranges from 80° to 90°. Thus, when the laser beam irradiates the inside of the flow chamber and after the light beam is reflected on the inner surface of the flow chamber, the reflected light is deviated from the optical axis (the propagation direction of laser beam), thereby reducing the luminous flux of the reflected light entering the laser. Those skilled in the art can understand that the angle θ is applicable to the present application as long as it would not cause the light reflected on the light incident surface of the flow chamber to enter the front light module. Through in-depth researches, it was found that although the oblique placement of the flow chamber may cause deviation of the optical path of forward scattered light and change of the collection angles of fluorescence and side scattered light, by further in-depth researches, it was found that it is possible to compensate for the influence of the forward scattered light by adjusting the position of the rear optical assembly in the optical path, and meanwhile, it has been proved through a large number of research experiments this is acceptable for the detection of the fluorescence and side scattered light, without affecting final detection results.

In the above-mentioned embodiments of the present disclosure, platelet particles are relatively small and generate small pulses when flowing through the flow chamber, as the reflected light generated by the laser beam when propagating in the optical path can be commendably isolated by the optical isolator in the optical detection system in the above-mentioned blood cell analyzer, the laser can stably output a laser beam, thereby avoiding small pulses occurring due to power peaks generated when the reflected light enters the laser, also avoiding confusion between the interfering small pulses and the small pulses generated by platelet particles, and greatly improving the detection precision.

An embodiment of the present disclosure also provides a platelet detection method applied to the above-mentioned blood cell analyzer comprising an optical detection system, wherein the optical detection system comprises a laser, a front optical assembly comprising an optical isolator, a rear optical assembly, a flow chamber and a first detector. The method comprises: providing a test sample solution containing platelets; making platelet particles in the test sample solution pass through a detection area of the flow chamber one by one; performing front optical treatment on a laser beam emitted by the laser by using the front optical assembly such that the laser beam subjected to the front optical treatment is converged at the detection area of the flow chamber in a first direction and scattered light is generated when the platelet particles pass through the detection area; performing rear optical treatment on the scattered light by using the rear optical assembly such that the scattered light subjected to the rear optical treatment enters the first detector, wherein reflected light generated when the laser beam passes through the flow chamber and the rear optical assembly is isolated by the optical isolator; and performing light intensity detection on the incident scattered light by using the first detector to obtain a first detection result so as to identify the platelet particles based on the first detection result.

In an embodiment, the method further comprises: performing hemolysis treatment on the collected blood sample, such that red blood cells in the blood sample are lysed to obtain a test sample solution containing a plurality of platelet particles.

In an embodiment, the method further comprises: performing front optical treatment on the laser beam by using the front optical assembly such that the laser beam subjected to the front optical treatment is converged at a blocking diaphragm included by the rear optical assembly in a second direction.

In an embodiment, the blood cell analyzer further comprises a second detector; correspondingly, the method further comprises: performing light intensity detection on the scattered light which forms an angle within a preset angle range with the propagation direction of the laser beam to obtain a second detection result, thereby identifying the platelet particles based on the first detection result and the second detection result.

In an embodiment, the blood cell analyzer further comprises a fluorescence detector; correspondingly, the method further comprises: performing staining treatment on the platelet particles in the test sample solution by using a specific fluorescence dye, wherein the specific fluorescence dye may be at least one of a membrane dye and a mitochondrion dye. Fluorescence is also generated when the platelet particles in the test sample solution pass through the detection area, and the fluorescence detector is configured to detect the fluorescence generated by the platelet particles to obtain a third detection result, thereby identifying the platelet particles based on the first detection result and the third detection result.

In an embodiment, the blood cell analyzer further comprises a second detector and a fluorescence detector; correspondingly, the method further comprises: performing fluorescence staining treatment on the platelet particles in the test sample solution; further generating fluorescence when the platelet particles in the test sample solution pass through the detection area; configuring the second detector to perform light intensity detection on the scattered light which forms an angle within a preset angle range with the propagation direction of the laser beam to obtain a second detection result, wherein the preset angle range may be 60° to 120°; configuring the fluorescence detector to detect the fluorescence generated by the platelet particles to obtain a third detection result; identifying the platelet particles and obtaining white blood cell count and classification based on the first detection result, the second detection result and the third detection result.

By applying the above-mentioned embodiments of the present disclosure, the reflected light generated when the laser beam propagates in the optical path can be commendably isolated such that the laser can stably output a laser beam, thereby avoiding small pulses occurring due to power peaks generated when the reflected light enters the laser, and also avoiding confusion between the interfering small pulses and the small pulses generated by platelet particles when the blood cells to be tested are platelets, and greatly improving the detection precision of the blood cell analyzer.

The optical detection system in the embodiments of the present disclosure comprises an optical subsystem, a flow chamber and a first detector, and the optical subsystem comprises a laser, a front optical assembly comprising an optical isolator, and a rear optical assembly comprising a blocking diaphragm, wherein the laser is configured to emit a laser beam; the front optical assembly is configured to perform front optical treatment such that the laser beam subjected to the front optical treatment is converged at the blocking diaphragm in a second direction and is converged at the blood cell sample to be tested at the blocking diaphragm in a first direction, and scattered light is thus generated; the rear optical assembly is disposed downstream of the flow chamber along the propagation direction of the laser beam, and is configured to perform rear optical treatment on the scattered light, such that the scattered light subjected to the rear optical treatment enters the first detector for light intensity detection; and the optical isolator is configured to isolate reflected light that is generated when the laser beam passes through the flow chamber and the rear optical assembly. Thus, the reflected light generated when the laser beam propagates in the optical path can be commendably isolated such that the laser can stably output a laser beam, thereby avoiding small pulses occurring due to power peaks generated when the reflected light enters the laser, and also avoiding confusion between the interfering small pulses and the small pulses generated by platelet particles when the blood cells to be tested are platelets, and greatly improving the detection precision of the blood cell analyzer.

The contents described above are only some specific embodiments of the present disclosure, but the protection scope of the present disclosure is not limited thereto. Any modifications or replacements, which can be easily obtained by one skilled in the art within the technical scope disclosed by the present disclosure, should fall within the protection scope of the present disclosure. Therefore, the protection scope of the present disclosure depends on the protection scope of the claims.

The invention claimed is:

1. A blood cell analyzer, comprising: a sampling part, a reaction part, an optical detection system, an analyzer and an output part, wherein the optical detection system comprises an optical subsystem, a flow chamber and a first detector;
   the sampling part comprises a sampling needle for collecting a blood sample and conveying the collected blood sample to the reaction part;
   the reaction part comprises a reaction cell and a reagent supply component, such that the blood sample reacts with a reagent to obtain a test sample solution containing a plurality of platelet particles, and the platelet particles flow through the flow chamber one by one;
   the optical subsystem comprises a laser, a front optical assembly and a rear optical assembly, and the front optical assembly comprises an optical isolator, wherein the laser is configured to emit a laser beam;
   the flow chamber is configured to allow the platelet particles to pass through in a line;
   the front optical assembly is configured to perform front optical treatment on the laser beam, and the laser beam subjected to the front optical treatment is converged at the platelets in the flow chamber in a first direction, and scattered light is thus generated;
   the rear optical assembly is disposed downstream of the flow chamber along the propagation direction of the laser beam, and is configured to perform rear optical treatment on the scattered light, such that the scattered light subjected to the rear optical treatment enters the first detector for light intensity detection;
   the optical isolator is configured to isolate reflected light from the laser, wherein the reflected light is generated when the laser beam passes through the flow chamber and the rear optical assembly;
   the analyzer is configured to detect the platelet particles flowing through the flow chamber according to light intensity signals of the scattered light obtained by the first detector, and thus obtain a detection result corresponding to the platelet particles; and
   the output part is configured to output the detection result corresponding to the platelet particles.

2. The blood cell analyzer of claim 1, wherein the optical isolator comprises a beam splitter prism and a polarization conversion element which are adhesively connected with each other;
   the beam splitter prism is configured to reflect the S-polarization component of the incident laser beam and transmit the P-polarization component of the incident laser beam;
   the polarization conversion element is configured to change the polarization state of the P-polarization component transmitted through the beam splitter prism such that the P-polarization component is changed from linearly polarized light into circularly polarized light, as well as to change the polarization state of the circularly polarized light after reflection into S-polarized light such that the S-polarized light is reflected by the beam splitter prism; or
   wherein the optical isolator comprises a polarization analyzer and a polarization conversion element which are adhesively connected with each other;
   the polarization analyzer is configured to allow only the P-polarization component of the laser beam to pass through;
   the polarization conversion element is configured to change the polarization state of the P-polarization component passing through the polarization analyzer such that the P-polarization component is changed from linearly polarized light into circularly polarized light, as well as to change the polarization state of reflected light of the circularly polarized light into S-polarized light such that the S-polarized light is isolated by the polarization analyzer.

3. The blood cell analyzer of claim 2, wherein the polarization conversion element is one of the following: a quarter wave plate and a magneto-optical crystal.

4. The blood cell analyzer of claim 1, wherein
   when the laser beam is incident to the optical isolator perpendicularly, the reflectivity of the first incident surface of the optical isolator is not greater than 0.5%.

5. The blood cell analyzer of claim 1, wherein the optical isolator comprises a bandpass filter and a frequency-doubling crystal which are adhesively connected with each other;
   the bandpass filter is configured to allow the laser beam with a wavelength X to pass through; and
   the frequency-doubling crystal is configured to perform frequency doubling on the laser beam passing through the bandpass filter and perform frequency doubling again on reflected light of the frequency-doubled laser beam, such that the reflected light is filtered out by the bandpass filter.

6. The blood cell analyzer of claim 1, wherein the front optical assembly further comprises a collimating lens; and
   the collimating lens is disposed between the laser and the optical isolator along the propagation direction of the laser beam, and is configured to collimate the laser beam to make the laser beam become a parallel beam.

7. The blood cell analyzer of claim 1, wherein the rear optical assembly further comprises a blocking diaphragm; and
   the front optical assembly is further configured to perform front optical treatment on the laser beam such that the laser beam subjected to the front optical treatment is converged at the blocking diaphragm in a second direction.

8. The blood cell analyzer of claim 7, wherein the front optical assembly further comprises a first light converging element and a second light converging element;
   the first light converging element is configured to perform first focusing on the laser beam such that the laser beam is converged in the first direction at the blood cell sample to be tested in the flow chamber, and scattered light is generated; and the second light converging element is configured to perform second focusing on the laser beam such that the laser beam is converged at the blocking diaphragm in a second direction.

9. The blood cell analyzer of claim 7, wherein
the second direction is perpendicular to the flow direction of the blood cell sample to be tested; and
the first direction is the same as the flow direction of the blood cell sample to be tested.

10. The blood cell analyzer of claim 7, wherein the blocking diaphragm has a light collection angle of 1-10°.

11. The blood cell analyzer of claim 1, wherein the rear optical assembly further comprises a third converging element and an aperture diaphragm; and
the third converging element is configured to perform third focusing on the scattered light such that the scattered light is converged at the aperture diaphragm and enters the first detector via the aperture of the aperture diaphragm.

12. The blood cell analyzer of claim 11, wherein the third light converging element is one of the following:
a lens assembly including at least one plano-convex lens and at least one biconvex lens;
a lens assembly including at least two plano-convex lenses;
a lens assembly including at least two biconvex lenses;
a lens assembly including at least two spherical lenses; and
an aspherical lens.

13. The blood cell analyzer of claim 1, wherein the optical detection system further comprises a second detector and/or a fluorescence detector;
the second detector is configured to perform light intensity detection on the scattered light which forms an angle within a preset angle range with the propagation direction of the laser beam; and
the fluorescence detector is configured to detect fluorescence generated by the blood cell sample to be tested.

14. The blood cell analyzer of claim 13, wherein the analyzer is further configured to detect the platelet particles in the flow chamber according to at least one of the following information and thus obtain a detection result corresponding to the platelet particles, the detection result including:
light intensity signals of the scattered light obtained by detection of the second detector; and
fluorescence intensity signals obtained by detection of the fluorescence detector.

15. The blood cell analyzer of claim 1, wherein the reaction part is further configured to perform hemolysis treatment on the collected blood sample, such that red blood cells in the blood sample are lysed to obtain a test sample solution containing a plurality of platelet particles.

16. The blood cell analyzer of claim 1, wherein the included angle between the propagation direction of the laser beam and the light incident surface of the flow chamber is a non-perpendicular angle.

17. The blood cell analyzer of claim 1, wherein the optical isolator has an optical isolation degree not smaller than 30 db.

18. The blood cell analyzer of claim 1, wherein the laser beam has a wavelength of 630 nm to 640 nm.

19. The blood cell analyzer of claim 1, wherein the laser beam is P-linearly polarized light.

20. The blood cell analyzer of claim 7, wherein the rear optical assembly further comprises a third converging element and an aperture diaphragm;
the third converging element is configured to perform third focusing on the scattered light such that the scattered light is converged at the aperture diaphragm and enters the first detector via the aperture of the aperture diaphragm; and
the blocking diaphragm is disposed between the flow chamber and the third converging element along the propagation direction.

21. The blood cell analyzer of claim 8, wherein the optical isolator is disposed between the laser and the first light converging element and the second light converging element along the propagation direction.

* * * * *